US007118905B2

(12) United States Patent
Chang et al.

(10) Patent No.: US 7,118,905 B2
(45) Date of Patent: Oct. 10, 2006

(54) NUCLEIC ACID ENCODING ANGIOGENESIS INHIBITOR

(75) Inventors: Jihoon Chang, Seoul (KR); Jang Seong Kim, Suwon-si (KR); Eun Jeong Park, Sungnam-si (KR); Jung-sun Yum, Sungnam-si (KR); Soo-il Chung, Sungnam-si (KR)

(73) Assignee: Mogam Biotechnology Research Institute, Yongin-si (KR)

( * ) Notice: Subject to any disclaimer, the term of this patent is extended or adjusted under 35 U.S.C. 154(b) by 19 days.

(21) Appl. No.: 10/849,961

(22) Filed: May 19, 2004

(65) Prior Publication Data

US 2004/0259202 A1 Dec. 23, 2004

Related U.S. Application Data

(63) Continuation of application No. 10/088,548, filed as application No. PCT/KR99/00554 on Sep. 15, 1999, now Pat. No. 6,743,428.

(51) Int. Cl.
*C12N 1/20* (2006.01)
*C12N 15/09* (2006.01)
*C12N 15/63* (2006.01)
*C07H 21/04* (2006.01)

(52) U.S. Cl. .............................. 435/252.3; 435/320.1; 536/23.5

(58) Field of Classification Search .............. 435/320.1, 435/252.3, 328; 536/23.5
See application file for complete search history.

(56) References Cited

U.S. PATENT DOCUMENTS

| | | | |
|---|---|---|---|
| 5,639,725 | A | 6/1997 | O'Reilly et al. |
| 5,801,012 | A | 9/1998 | Soff et al. |
| 5,945,403 | A | 8/1999 | Folkman et al. |
| 6,743,428 | B1 * | 6/2004 | Chang et al. ............. 424/185.1 |

OTHER PUBLICATIONS

Lou, X. J. et al., 1998, Despite Its Homology to Angiostatin Apolipoprotein(a) Does Not Affect Angiogenesis, *Exp. Mol. Pathol.*, 65:53-63.
LoGrasso, P. V. et al., 1994, Cloning, Expression, and Characterization of Human Apolipoprotein (a) Kringle IV37, *J. Biol. Chem.*, 269(34):21820-21827.
Scanu, A. M. and Edelstein, C., 1994, Apolipoprotein(a): structural and functional consequences of mutations in kringle type 10 (or kringle 4-37), *Clinical Genetics*, 46:42-45.
Scanu, A. M. et al., 1994, A single point mutation (Trp72→Arg) in human apo (a) kringle 4-37 associated with a lysine binding defect in Lp(a), Biochimica et Biophysica Acta, 1227:41-45.
Gabel, B. R. and Koschinsky, M. L., 1998, Sequences within Apolipoprotein(a) Kringle IV Types 6-8 Bind Directly to Low-Density Lipoprotein and Mediate Noncovalent Association of Apolipoprotein(a) and Apolipoprotein B-100, Biochemistry, 37:7892-7898.
Mikol V, et al., 1996, Crystal structures of apolipoprotein(a) kringle IV37 free and complexed with 6-aminohexanoic acid and with p-aminomethylebenzoid acid: existence of novel and expected binding modes. J Mol Biol. 256(4):751-61.
Burgess et al., 1990, Possible dissociation of the heparin-binding and mitogenic activities of heparin-binding growth factor-1 from its receptor-binding activites by site-directed mutagenesis of a single lysine residue. J Cell Biol. 111:2129-2138.
Bowie JU et al., 1990, Deciphering the message in protein sequences: tolerance to amino acid substitutions. Science. 247(4948):1306-1310.
Fogarty M., 2002, Learning from Angiogenesis Trial Failures. The Scientist 16:33.
Fan TP et al., 1995, Controlling the vasculature: angiogenesis, anti-angiogenesis and vascular targeting of gene therapy. Trends Pharmacol Sci. 16:57-66.
Wallace RW, 1998, Media hype and drug discovery Drug Discovery Today, 3(10):433-434.
Cao Y et al., 1997, Kringle 5 of plasminogen is a novel inhibitor of endothelial cell growth. J Biol Chem. 272:22924-22928.
Kraft HG et al., 1995, Sequence polymorphism in kringle IV 37 in linkage disequilibrium with the aopolipoprotein (a) size polymorphism Hum Genet. 95(3):275-282.
McLean et al., 1987, cDNA sequence of human apolipoprotein(a) is homologous to plaminogen. Nature 330(6144):132-7.

* cited by examiner

*Primary Examiner*—Maher M. Haddad
(74) *Attorney, Agent, or Firm*—Joseph Hyosuk Kim; JHK Law

(57) ABSTRACT

The present invention provides a novel angiogenesis inhibitor, LK68 whose amino acid sequence is identical with the human apolipoprotein (a) kringle domains IV36, IV37 and V38, a cDNA sequence encoding the LK68, a recombinant expression vector comprising the cDNA, a recombinant microorganism transformed with the recombinant expression vector and a novel use of the LK68 as an anticancer agent and a method for treating angiogenesis-mediated disease. LK68, LK6, LK7 and LK8 exhibit inhibitory activities on the cultured endothelial cell proliferation as well as on the endothelial cell migration. LK68 and its single kringles also inhibit the normal development of capillaries in the chick embryo chorioallantoic membrane (CAM). It was also showed that systemic administration of LK68 causes the inhibition of primary tumor growth, which is correlated with a suppression of tumor-induced angiogenesis. Accordingly, LK68 protein, its single kringles or their functional equivalents may be applied for the development of a potent anti-cancer agent, which is highly effective for angiogenesis-mediated diseases covering cancer, rheumatoid arthritis, psoriasis, ocular angiogenic disease, etc.

20 Claims, 12 Drawing Sheets

NUCLEIC ACID ENCODING ANGIOGENESIS INHIBITOR

CROSS-REFERENCE TO RELATED APPLICATIONS

The present application is a continuation application of U.S. patent application Ser. No. 10/088,548, filed on Mar. 15, 2002, now U.S. Pat. No. 6,743,428, U.S. patent application No. 10/088,548 was filed under 35 U.S.C. 371, U.S. national phase application of PCT/KR99/00554, filed on Sep. 15, 1999, the contents of which are incorporated by reference herein in its entirety.

BACKGROUND OF THE INVENTION

1. Field of the Invention

The present invention relates to a novel angiogenesis inhibitor, LK68 whose amino acid sequence is identical with the human apolipoprotein(a) kringle domains IV36, IV37 and V38, more specifically, to an amino acid sequence of the LK68, a cDNA sequence encoding the LK68, a recombinant expression vector comprising the cDNA, a recombinant microorganism transformed with the recombinant expression vector and a novel use of the LK68 as an anticancer agent and a method for treating the angiogenesis-mediated disease.

2. Description of the Prior Art

Angiogenesis is a biological process of generating new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. It has been reported that new vessel growth is tightly controlled by many angiogenic regulators (see: Folkman, J., Nature Med., 1: 27–31, 1995a), and the switch of the angiogenesis phenotype depends on the net balance between up-regulation of angiogenic stimulators and down-regulation of angiogenic suppressors.

An imbalance of the angiogenic process has been shown to contribute to pathological disorders such as diabetic retinopathy, rheumatoid arthritis and psoriasis (see: Folkman, J., Nature Med., 1: 27–31, 1995a). Especially, both primary and metastatic tumors need to recruit angiogenic vessels for their growth (see: Folkman, J., New Engl. J. Med., 285:1182–1186, 1971; Folkman, J., J. Biol. Chem., 267:10931–10934, 1992). If this angiogenic activity could be repressed or eliminated, then the tumor, although present, would not grow. There are many reports suggesting that inhibiting tumor angiogenesis should provide a practical approach to long term control of the disease. Blocking positive regulators of angiogenesis or utilizing negative regulators to suppress angiogenesis results in a delay or regression of experimental tumors. If the angiogenic activity could be repressed or eliminated, then the tumor, although present, would not grow. Moreover, in the disease state, prevention of angiogenesis could avert the damage caused by the invasion of the new microvascular system effectively. Therefore, therapies directed at control of the angiogenic process could lead to the abrogation or mitigation of these diseases.

Therefore, what is needed is a novel angiogenesis inhibitor which can inhibit the unwanted growth of blood vessels, especially into tumors. An anticancer agent comprising the angiogenesis inhibitor should be able to overcome the activity of endogenous growth factors in premetastatic tumors and prevent the formation of the capillaries in the tumors thereby inhibiting the growth of the tumors. The anticancer agent should also be able to modulate the formation of capillaries in other angiogenic processes, such as wound healing and reproduction. Finally, the anticancer agent and method for inhibiting angiogenesis should preferably be non-toxic and produce few side-effects.

Until now, at least 10 endogenous angiogenic inhibitors have been identified in the art (see: O'Reilly, M. S. et al., Cell, 88: 277–285, 1997). One such molecule is angiostatin, which consists of the plasminogen kringle I through IV(see: O'Reilly, M. S. et al., Cell, 79:315–328, 1994). When applied systemically, angiostatin powerfully inhibits both primary tumor growth and metastasis without toxicity, and angiogenesis induced by bFGF as well (see: O'Reilly, M. S. et al., Nature Med., 2:689–692, 1996). These anti-tumor effects were accompanied by a marked reduction of microvessel density within the tumor mass, indicating that suppression of angiogenesis was associated with the inhibition of tumor growth.

Kringles are protein structural domains composed of approximately 80 amino acids and three intramolecular disulfide bonds. Kringle structures are found in many proteins such as prothrombin (see: Walz, D. A. et al., Proc. Natl. Acad. Sci., U.S.A., 74:1969–1973, 1977), plasminogen(see: Ponting, C. P., Blood Coagul. & Fibrinolysis, 3:605–614, 1992), urokinase(see: Pennica, D. et al., Nature, 301:579–582 1983), hepatocyte growth factor(see: Lukker, N. A. et al., Protein Eng., 7:895–903, 1994), and apolipoprotein("apo")(a)(see: McLean, J. W. et al., Nature, 330: 132–137, 1987). These domains appear to be independent folding units, but their functional role is not yet known. The previous reports represent that the kringle structure can act as inhibitors of endothelial cell migration and proliferation during angiogenesis. Specifically, prothrombin's kringle 2 and plasminogen's kringle 1–4, and 5 have been shown to be anti-angiogenic(see: Ji, W. R. et al., FASEB J., 15:1731–1738, 1998a; Ji, W. R. et al., Biochem. Biophys. Res. Commun., 247:414–419, 1998b; Cao, Y. et al., J. Biol. Chem., 271:29461–29467, 1996; Cao, Y. et al., J. Biol. Chem., 272:22924–22928, 1997; Barendsz-Janson, A. F., J. Vasc. Res., 35:109–114, 1998; Lee, T. H. et al., J. Biol. Chem., 273:28805–28812, 1998).

Apolipoprotein(a), one of the proteins having kringle structures, is a candidate for a novel angiogenesis inhibitor. Apo(a) is covalently attached to apoB-100, the main protein component of low density lipoprotein(LDL) to form lipoprotein(a) (see: Fless, G. M., J. Biol. Chem., 261: 8712–8718, 1986). Elevated plasma concentration of Lp(a) represents a major independent risk factor for artherosclerosis(see: Armstrong, V. W. et al., Artherosclerosis, 62:249–257, 1986; Assmann, G., Am. J. Cardiol., 77:1179–1184, 1996; Bostom, A. G. et al., JAMA, 276: 544–548, 1996). Although several pathogenic activities have been reported, the physiological role of apo(a) has not yet been established(see: Lawn, R. M. et al., J. Biol. Chem., 271:31367–31371, 1996; Scanu, A. M. and Fless, G. M., J. Clin. Invest., 85:1709–1715, 1990; Utermann, G., Science, 246:0904–910, 1989).

Apo(a) contains two types of kringle domains and an inactive protease-like domainsee: the first 37 kringle domains are ~75% identical to plasminogen kringle IV, and the last kringle domain is 90% identical to plasminogen kringle V. Interestingly, the kringle IV-like domain is present in 15–40 copies in different human alleles of the apo(a)

gene. In this regard, it is feasible to develop an inhibitor of tumor angiogenesis and growth employing the Apo(a) kringle structures.

SUMMARY OF THE INVENTION

In accordance with the present invention, the inventors have cloned and expressed the human apo(a) kringles containing IV36, IV37 and V38 as a recombinant protein LK68, and discovered that: the LK68 protein and its single kringles, LK6, LK7 and LK8, have an ability to overcome the angiogenic activity of endogenous growth factors such as bFGF in vitro; and they may be used as active ingredients of anticancer agents.

The first object of the invention is, therefore, to provide a novel LK68 protein consisting of human apo(a) kringle domains IV36, IV37 and V38, and cDNA encoding the LK68 protein.

The second object of the invention is to provide a novel recombinant vector containing the cDNA encoding human apo(a) kringle domains IV36, IV37 and V38.

The third object of the invention is to provide an anticancer agent which comprises the LK68 protein or its single kringles, LK6, LK7 and LK8, as an active ingredient.

The fourth object of the invention is to provide a method for treating angiogenesis-mediated disease by employing the LK68 protein.

BRIEF DESCRIPTION OF THE DRAWINGS

The above and the others objects and features of the present invention will become apparent from the following description given in conjunction with the accompanying drawings, in which.

DETAILED DESCRIPTION OF THE INVENTION

Figure 1:
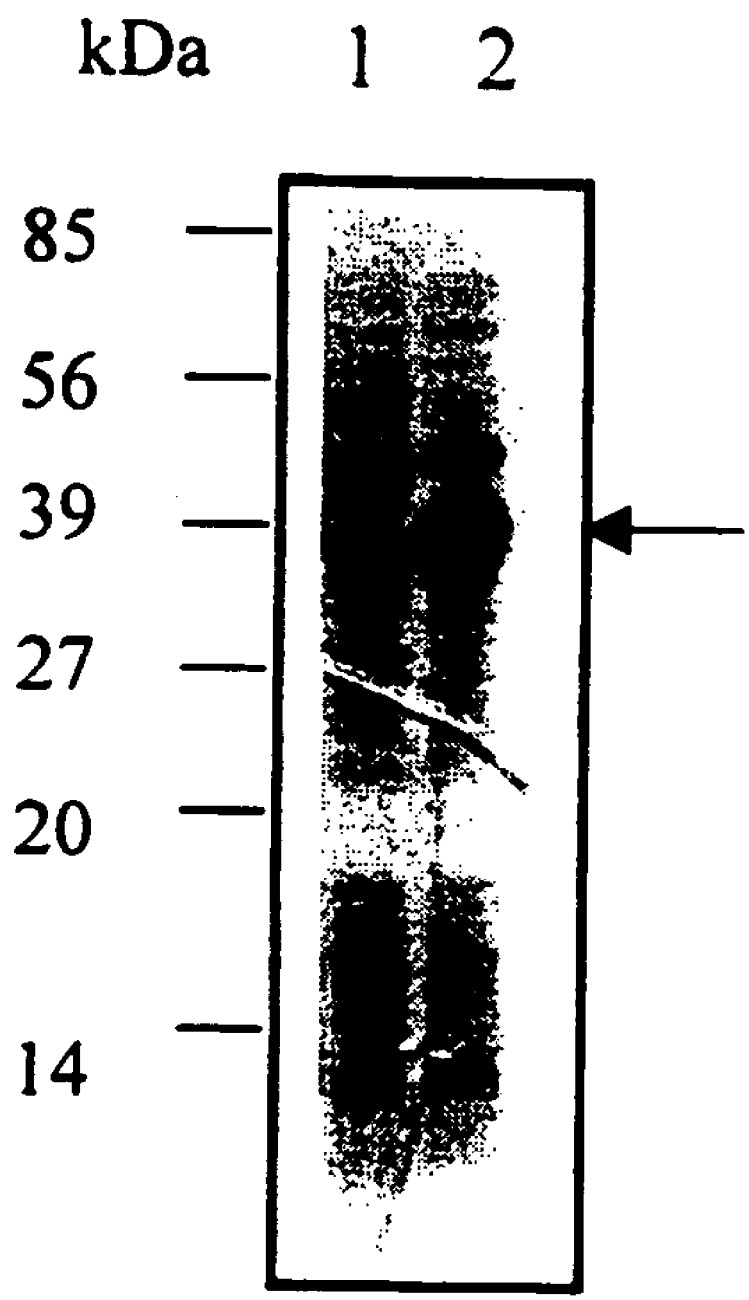
FIG. 1 is a photograph of a SDS-polyacrylamide gel electrophoresis for analysis of recombinant LK68 protein expressed in E. coli.

The present invention provides a novel protein LK68, which can be cloned and expressed as recombinant protein from the human apolipoprotein("apo")(a) kringles. The LK68 protein consists of amino acid sequences of human apolipoprotein(a) kringle domains IV36(amino acid 8 to 80), IV37(amino acid 122 to 194) and V38(amino acid 226 to 300) in a serial manner(see: SEQ ID NO: 2). The first two kringle domains of LK68 (i.e., IV36 and IV37) are homologous to human plasminogen kringle IV, and the third kringle domain V38 is homologous to human plasminogen kringle V. The present invention also provides a cDNA encoding the LK68 protein (see: SEQ ID NO: 1) and recombinant vectors which comprises the said cDNA and expression vectors such as pET vector series.

In describing the kringle domains of the invention, human apolipoprotein(a) kringles IV36, IV37 and V38 are abbreviated as KIV36, KIV37 and KV38, respectively; LK68 is employed to mean the recombinant protein which comprises the said three kringle domains; and, LK6, LK7 and LK8 are employed to mean the recombinant proteins of KIV36, KIV37 and KV38, respectively.

Because apolipoprotein(a) contains plasminogen-type IV and V kringle domains, it was assumed that apolipoprotein (a) could possibly have an anti-angiogenic activity. There is an experimental evidence suggesting apolipoprotein(a) may contain biological activity as an inhibitor of tumor angiogenesis and growth(see: Trieu, V. N. and Uckun, F. M., Biochem. Biophys. Res. Commun., 257:714, 1999). It has been reported that LL/2(Lewis Lung Carcinoma) tumor growth is delayed in apo(a) transgenic mice and the microvessel density of LL/2 tumors from apo(a) transgenic mice is lower than that from wild-type mice as control.

Under the circumstance, the present inventors assumed that LK68 protein, its single kringles or their functional equivalents may have an anti-angiogenic activity. To verify said anti-angiogenic activity, it was investigated whether recombinant LK68 and its single kringles (i.e., LK6, LK7 and LK8) are potent anti-angiogenic factors in vitro and in vivo as well. As a result, LK68, LK6, LK7 and LK8 exhibit inhibitory activities on the cultured endothelial cell proliferation as well as on the endothelial cell migration. LK68 and its single kringles also inhibit the normal development of capillaries in the chick embryo chorioallantoic membrane (CAM). It was also shown that systemic administration of LK68 inhibited the primary tumor growth, which is correlated with a suppression of tumor-induced angiogenesis. Since each of the single kringle proteins, LK6, LK7 and LK8 showed anti-angiogenic activity, it is expected that they also inhibit the primary tumor growth or metastasis.

Accordingly, LK68 protein, its single kringles or their functional equivalents may be applied for the development of a potent anti-cancer agent, which is highly effective for angiogenesis-mediated diseases covering reumatoid arthritis, psoriasis, or ocular angiogenic diseases, etc.

Also, LK68 protein, its single kringles or their functional equivalents may be used in combination with other compositions and procedures for the treatment of diseases. For example, tumor may be treated conventionally with surgery, radiation or chemotherapy combined with LK68, its single kringles, or their functional equivalent, and then LK68, its single kringles, or their functional equivalent may be subsequently administered to the patient to extend the dormancy of micrometastases and to stabilize and inhibit the growth of any residual primary tumor.

The present invention is further illustrated in the following examples, which should not be taken to limit the scope of the invention.

EXAMPLE 1

Cloning and Expression of Recombinant LK68

In order to verify the anti-angiogenic activity of human apo(a) kringle, the inventors cloned and expressed the last three kringles containing IV36, IV37 and V38 as a recombinant protein LK68. A DNA fragment of apo(a) spanning nucleotides 12,052 to 12,975(see: McLean J. W. et al., Nature, 330:132, 1987) was PCR-amplified from human liver cDNA and the resulting 924-bp NdeI-BamHI fragment was ligated into E.coli expression vector pET11a(Novagen, USA). The oligonucleotide primers A(SEQ ID NO: 9)and F(SEQ ID NO: 14) (see: Table 1) were used for PCR amplification under the standard PCR protocol. This clone was named "pET11a/LK68", which encodes 308 amino acids including human apo(a) kringle domains, IV36, IV37 and V38(see: SEQ NO ID: 2). The first two kringle domains of this clone, IV36 and IV37, are homologous to human plasminogen kringle IV, and the third kringle domain V38 is homologous to human plasminogen kringle V.

The nucleotide sequences of this clone were confirmed in both directions. When the nucleotide sequence of this clone was compared to the same region of the human apo(a)(see: McLean J. W. et al., Nature, 330:132, 1987), the nucleotide sequences are identical with the exception of a single base change at nucleotide 554. Our clone contains a cytosine at this position as compared to a thymidine in the sequence reported by McLean et al.(see: McLean J. W. et al., Nature, 330:132, 1987), causing an amino acid change to Thr from Met. This substitution has also been reported by other groups(see: Van der-Hoek, Y. Y. et al., Hum. Mol. Genet., 2:361–366, 1993; LoGrasso, P. V. et al., J. Biol. Chem., 269:21820–21827, 1994) and appears to be the predominant allele for apo(a).

E. coli BL21(DE3) was transformed with an expression plasmid pET11a/LK68 and recombinant LK68 protein was expressed under the following conditions. One liter of Luria-Bertani broth containing ampicillin was inoculated with 10 ml of an overnight culture of E. coli BL21(DE3) harboring the pET11a/LK68 plasmid and incubated with shaking at 37° C. When the $OD_{600}$ of the culture reached 0.4–0.6, isopropylthio-β-D-galactoside(IPTG) was added at a final concentration of 1 mM. Cells were grown an additional 4 h after induction. Cells were harvested by centrifugation at 8000×g for 30 min at 4° C. These cell pellets were sonicated and the over-expressed proteins were analyzed by SDS-PAGE(see: FIG. 1). In FIG. 1, Mr represents a molecular weight marker(Boehringer Mannheim, Germany); lane 1, the expression of recombinant LK68 protein without IPTG induction; and, lane 2, the expression of recombinant LK68 protein with IPTG induction, respectively. Recombinant LK68 protein having a molecular weight of 37 kDa was well expressed in E. coli, accumulating to about 20–30% of the total protein, as evidenced by image analysis of the scanned gel. The transformant thus prepared was designated as 'Escherichia coli BL21/LK6–8', and deposited with the Korean Collection for Type Cultures, #52 Oun-dong, Yusong-ku, Taejon 305–333, Republic of Korea, an international depository authority as accession No. KCTC0633BP on Jun. 9, 1999.

Each of single kringle domains, IV36, IV37 and V38, was cloned separately into an expression vector pET15b as described above. The oligonucleotide primers used for cloning are listed in Table 1: that is, A(SEQ ID NO: 9) and D(SEQ ID NO: 12) for KIV36 cloning; B(SEQ ID NO: 10) and E(SEQ ID NO: 13) for KIV37 cloning; and, C(SEQ ID NO: 11) and F(SEQ ID NO: 14) for KV38 cloning, respectively. These three couples of oiligonucleotide primers were used for PCR amplification under the standard PCR protocol and the resulting clones were named "pET15b/LK6", "pET15b/LK7" and "pET15b/LK8", each of which includes the single human apo(a) kringle domains of IV36, IV37 and V38, respectively. E. coli BL21(DE3) competent cells were transformed with each of the expression plasmid, pET15b/LK6, pET15b/LK7 and pET15b/LK8. The transformant with plasmid pET15b/LK6 thus prepared was designated as 'Escherichia coli BL21(DE3)/LK6', and deposited with the Korean Collection for Type Cultures, #52 Oun-dong, Yusong-ku, Taejon 305–333, Republic of Korea, an international depository authority as accession No. KCTC0655BP on Sep. 3, 1999. The transformant with plasmid pET15b/LK7 thus prepared was designated as 'Escherichia coli BL21(DE3)/LK7', and deposited with the Korean Collection for Type Cultures on the same address as above, an international depository authority as accession No. KCTC0656BP on Sep. 3, 1999. The transformant with plasmid pET15b/LK8 thus prepared was designated as 'Escherichia coli BL21/LK8', and deposited with the Korean Collection for Type Cultures on the same address as above, an international depository authority as accession No. KCTC0634BP on Jun. 9, 1999.

Recombinant LK6, LK7 and LK8 proteins were expressed under the same conditions as fusion proteins containing N-terminal His-tag. Each of the over-expressed recombinant LK6, LK7 and LK8 protein was purified using pET His-tag system under the manufacturer's recommended condition.

TABLE 1

Oligonucleotide primers used for PCR cloning

| Nucleotide Sequences* | Description | Location** | SEQ ID NO. |
|---|---|---|---|
| A. TCCATATGAAAAGCCCTGTGGTCCAGGAT | K36-5' | 12052–12072 | 9 |
| B. CAGTCCATATGGTCCGCCAGTGCTACCATGGCA | K37-5' | 12406–12427 | 10 |

TABLE 1-continued

Oligonucleotide primers used for PCR cloning

| Nucleotide Sequences* | Description | Location** | SEQ ID NO. |
|---|---|---|---|
| C. GGAATTCCATATGAACAGGACTGCATGTTT | K38-5' | 12718–12735 | 11 |
| D. CGGGATCCTTAACCTGATTCTGTTTC | K36-3' | 12310–12323 | 12 |
| E. CGGGATCCTTAGACCACAGTCCCTTC | K37-3' | 12658–12671 | 13 |
| F. CGGGATCCTTAAGAGGATGCACA | K38-3' | 12964–12975 | 14 |

*Restriction sites, NdeI and BamHI are added for the cloning conveniences (underlined).
**See: McLean et al., Nature, 330:132, 1987, for nucleotide sequence (accession number is X06290).

EXAMPLE 2

Purification of the Recombinant LK68

In order to produce the recombinant LK68, high cell-density fermentation was performed in a 5 L Bioflow III bioreactor(New Brunswick Scientifics, Edison, USA) in the following medium: 4%(w/v) yeast extract, 4%(w/v) glycerol, 1%(w/v) dibasic sodium phosphate, 0.2%(w/v) monobasic potassium phosphate and 50 µg/ml ampicillin. When the cells reached an absorbance of 100 at 600 nm, protein expression was induced with 1 mM IPTG and then DO-stat fed-batch was carried out for 9 h with feed media (29%(w/v) yeast extract, 39%(w/v) glycerol and 0.5%(w/v) magnesium sulfate. Cells were harvested by centrifugation at 8000×g for 30 min. Each fermentation process yielded about 80 g of cell/L(wet weight).

To assess if LK68 was expressed in the soluble fraction or the insoluble cellular fraction of *E.coli* cells, the inventors analyzed the LK68 expression in these fractions. This analysis showed that LK68 was located in the insoluble cellular fraction. Thus, it was necessary to denature, refold and reoxidize the disulfied bonds of LK68. By using the deoxycholate and other detergents, the insoluble LK68 protein was purified as inclusion bodies to the extent of >95% purity. Then, the inclusion bodies were solublized with 7M urea and folded into native conformation using a rapid dilution and an equilibrium dialysis scheme. In the folding buffer, purified inclusion bodies were easily refolded without detectable protein aggregation. After the dialysis, the protein was purified by lysine-Sepharose 4B affinity chromatography. The protein bound to lysine-Sepharose was specifically eluted by ε-ACA(ε-amino-n-caproic acid). This suggested that the lysine-binding site located in the KIV37 kringle of the refolded protein was fully functional. Affinity elution of LK68 with 0.1M ε-ACA yielded about 3 mg of protein/g of cells(wet weight). Chromatography with polymyxin-B beads(Sigma Chemical Co., USA) was subsequently performed to eliminate any endotoxin, and residual endotoxin activity was determined with the *Limulus* amebocyte lysate assay kit(Biowhittaker Inc., USA). The purified protein was analyzed by SDS-PAGE and was stored at −20° C. until needed. The calculated pI value of LK68 protein is 6.13. The N-terminal amino acid sequence of the purified LK68 was confirmed by amino acid sequencing.

EXAMPLE 3

Chick Chorioallantoic Membrane Assay

Figure 2:
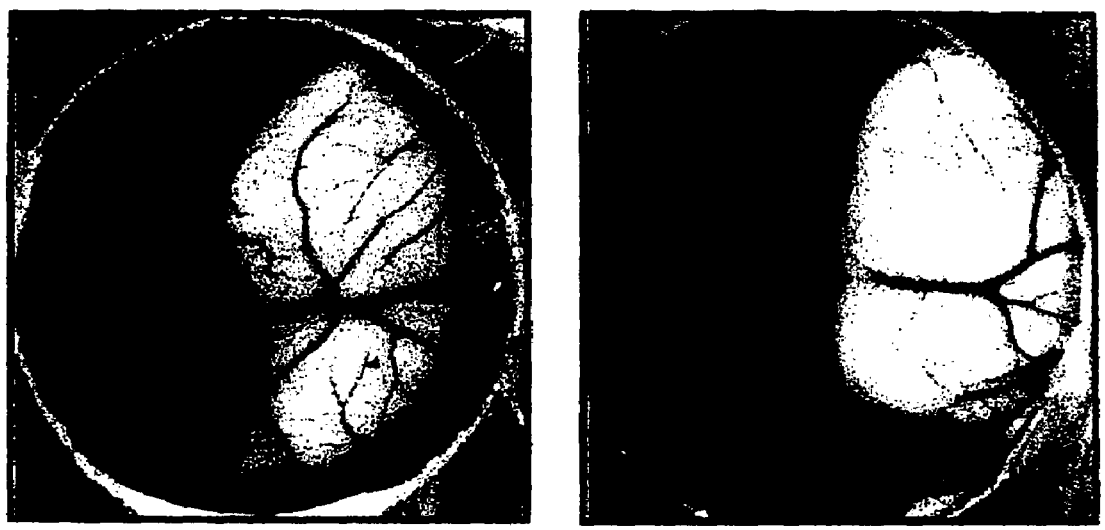
FIG. 2 is a photograph showing the inhibition of angiogenesis by LK68 on the chick chorioallantoic membrane (CAM).

In order to determine whether LK68 is anti-angiogenic in vivo, the inventors tested its ability to inhibit the development of capillaries in the chorioallantoic membrane ("CAM") (see: Lee, T. H. et al., J. Biol. Chem., 273: 28805–28812, 1998). Fertilized three-day-old eggs were incubated at 37° C., and a window was made after the extraction of ovalbumin. After two days of incubation, a Thermanox coverslip(Nunc Inc., USA) containing recombinant LK68 protein was applied to the CAM of individual embryos. After 48 h, 20% fat emulsion was injected into the chorioallantois of the embryos, and the vessel formation around the Thermanox was examined(see: FIG. 2). In FIG. 2, the left photograph shows the normal development of capillaries in the CAM; and, the right shows the inhibition of angiogenesis by LK68 on CAM, respectively.

Figure 3A:
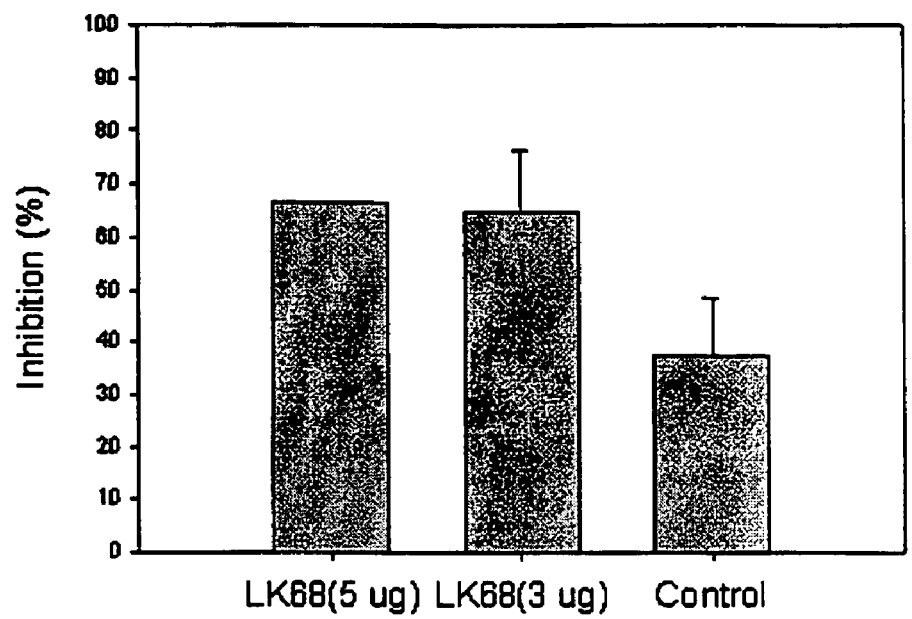
FIG. 3(A) is a graph showing inhibition of vessel growth in the CAM as a function of LK68.
Figure 3B:
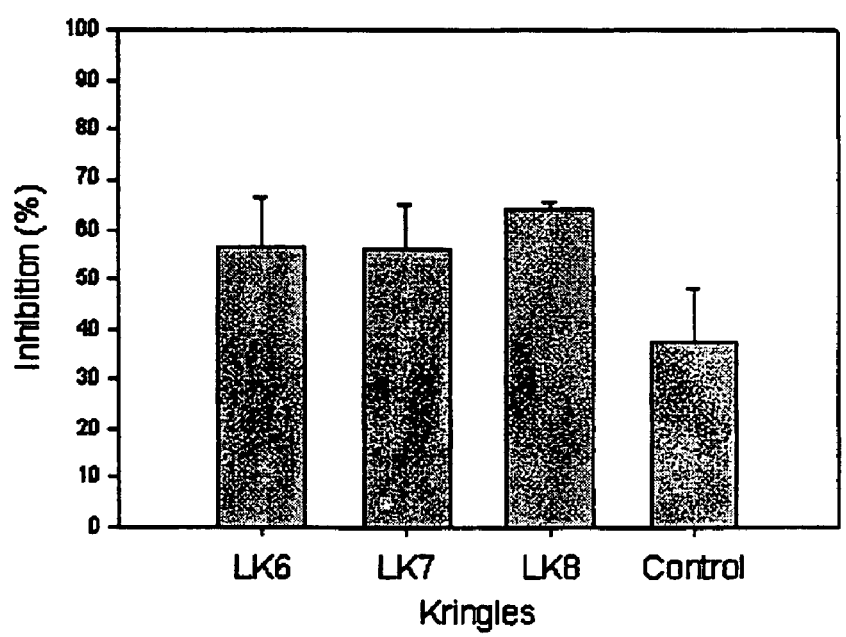
FIG. 3(B) is a graph showing inhibition of vessel growth in the CAM as a function of single kringles, LK6, LK7, LK8, and a control.

When LK68 at the dose range of 3–5 µg was applied on the CAM, more than 60% among the 100 eggs tested showed avascular zone around the sample applied, indicating that the growth of capillaries was inhibited. With the recombinant proteins of each kringle domain, e.g. LK6, LK7 or LK8, 60–70% of the eggs tested showed inhibitory effects at the dose range of 1 µg/CAM(see: FIGS. 3(A) and 3(B)). This in vivo study showed that apo(a) kringle domains have anti-angiogenic activity and LK68 as well as single kringle proteins is a potent inhibitor of angiogenesis. There was no evidence of toxicity in any of the chick embryos tested.

EXAMPLE 4

Inhibition of Endothelial Cell Proliferation

Recombinant LK68, LK6, LK7 and LK8 proteins were assayed for their inhibitory activity on proliferation of bovine capillary endothelial (BCE) cells stimulated by bFGF under the following conditions. BCE cells were grown in DMEM containing 10% bovine calf serum (BCS) and 3 ng/ml bFGF(Upstate Biotechnology, USA). Approximately 3,000 cells were added to each well of 96-well tissue culture plate and incubated at 37° C. in 5% $CO_2$ atmosphere. After incubation for 18 h, the medium was replaced with DMEM containing 0.5% BCS, and the test samples were added to each well. After 30 min incubation, bFGF was added to a final concentration of 1 ng/ml. The cell count was determined by [$^3$H]thymidine incorporation method. The experiments were performed in triplicate.

Figure 4A:
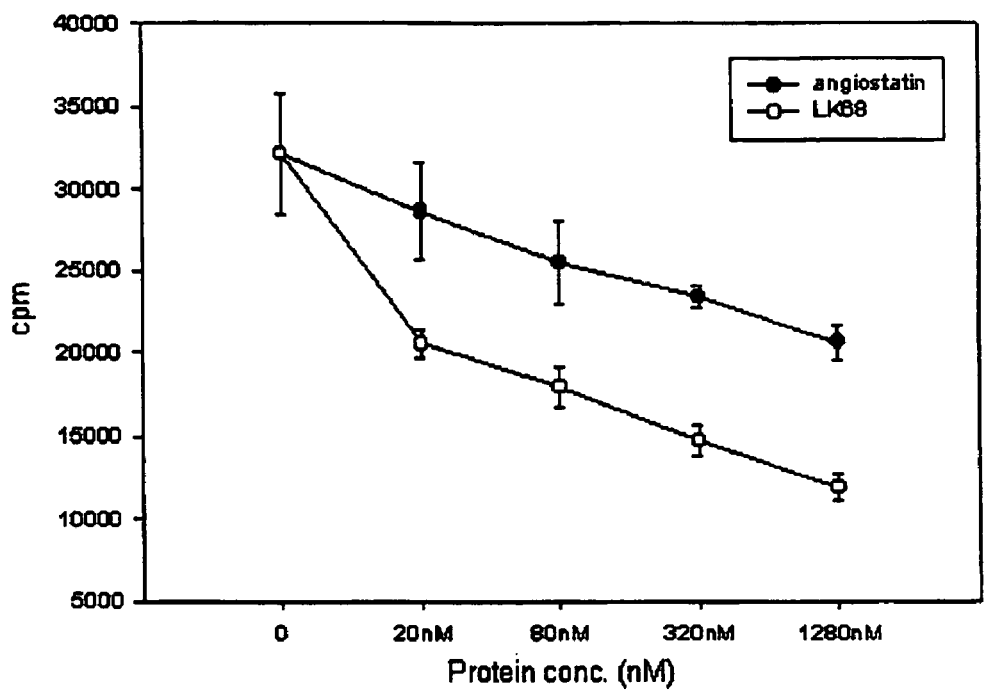
FIG. 4(A) is a graph showing inhibition of BCE cell proliferation by recombinant LK68 and angiostatin.
Figure 4B:
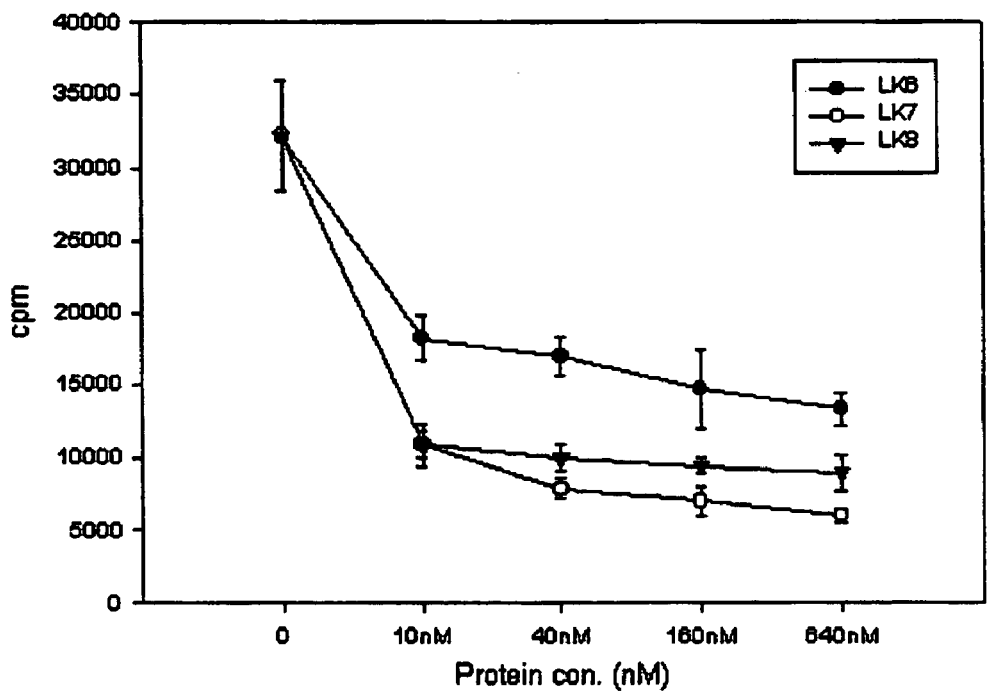
FIG. 4(B) is a graph showing inhibition of BCE cell proliferation by recombinant LK6, LK7 and LK8.

As can be seen in FIG. 4, it was determined that LK68, LK6, LK7 and LK8 specifically inhibited BCE cell proliferation in a dose-dependent manner. When the angiostatin was applied as a positive control, all the Apo(a) kringle proteins tested appeared to be more effective under the conditions used in this experiment. The concentration of half-maximal inhibition ($ED_{50}$) for LK68 is determined about 200–250 nM, about 140–170 nM for LK6, about 10–20 nM for LK7, and about 10–20 nM for LK8 (see: FIGS. 4(A) and 4(B)).

Recombinant LK68 and LK8 proteins were assayed for their inhibitory activity on proliferation of human umbilical vein endothelial (HUVEC) cells stimulated by bFGF under the following conditions. HUVECs(American Type Culture Collection, USA) were grown in F12K medium containing 10% heat-inactivated fetal bovine serum("FBS") (Hyclone, USA), 30 µg/ml endothelial cell growth supplement(ECGS) (Sigma Chemical Co., USA), and 100 µg/ml heparin(Sigma Chemical Co., USA). The cells were plated at a density of 2000/well in 96-well tissue culture plate. The cells were incubated at 37° C., 5% $CO_2$, for 18 hr, washed once with serum-free medium, and F12 medium containing 0.5% FBS was added. The cells were treated with various concentrations of samples and incubated for 30 min. Then, ECGS, heparin and bFGF(Upstate Biotechnology, USA) were added into the cells with the final concentrations of 30 µg/ml, 100 µg/ml and 5 ng/ml, respectively. After 48 hr of incubation, cell counts were determined with the Cell Proliferation ELISA using 5-bromo-2'-deoxyuridine (BrdU) (Boehringer Mannheim, USA). The experiments were performed in triplicate.

Figure 4C:
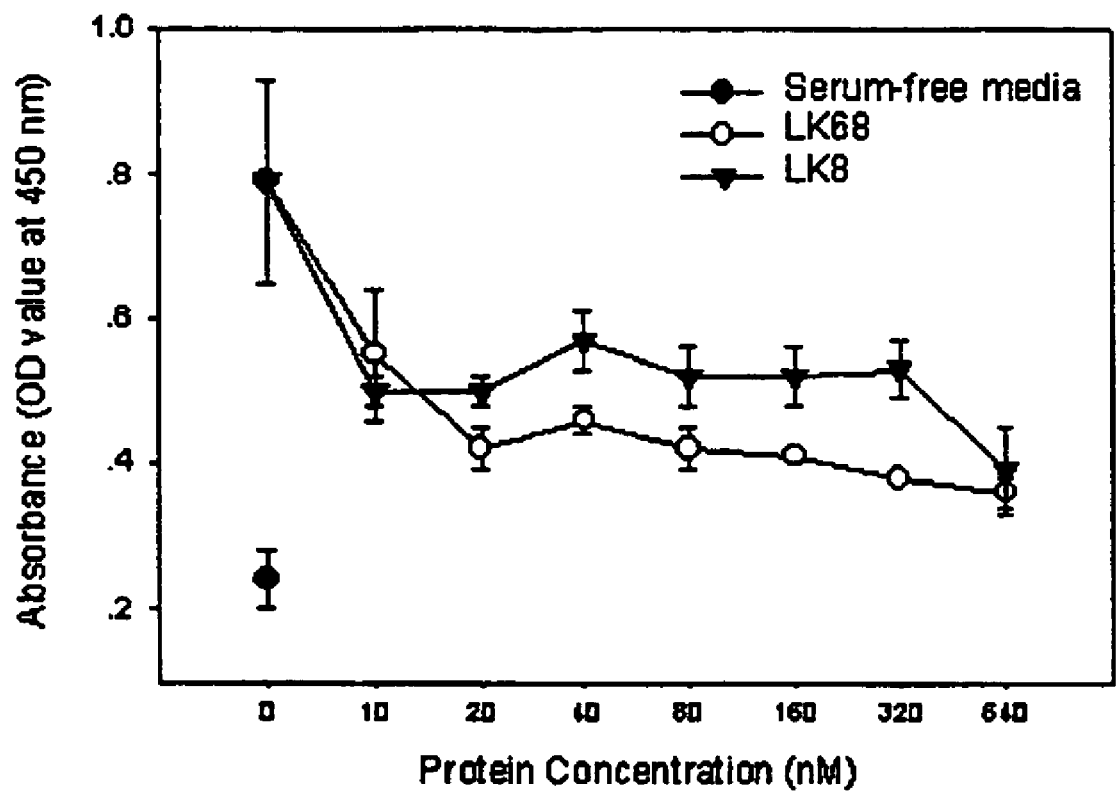
FIG. 4(C) is a graph showing inhibition of HUVEC cell proliferation by recombinant LK68 and LK8.

As can be seen in FIG. 4(C), it was determined that LK68 as well as LK8 specifically inhibited HUVEC cell proliferation in a dose-dependent manner.

Figure 5A:
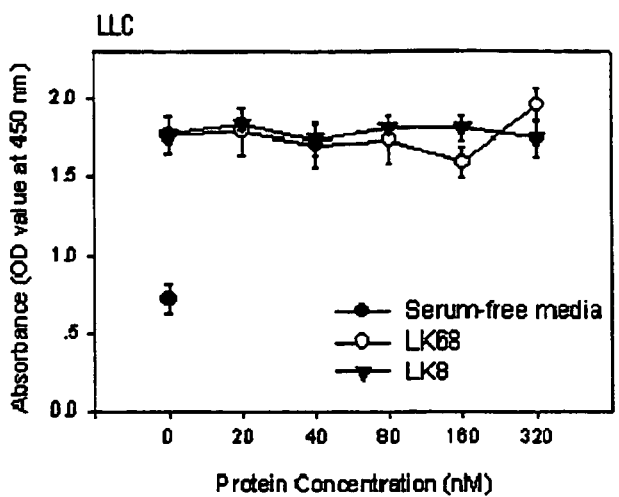
FIG. 5(A) is a graph showing BrdU labeling index of LLC cells in the presence of recombinant LK68 and LK8.
Figure 5B:
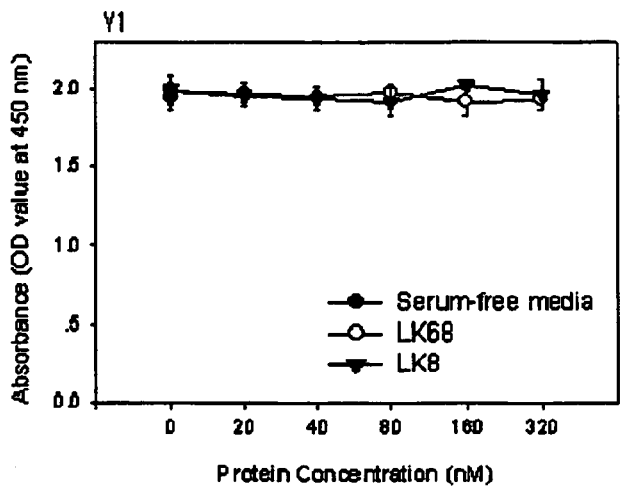
FIG. 5(B) is a graph showing BrdU labelling index of Y1 cells in the presence of recombinant LK68 and LK8.
Figure 5C:
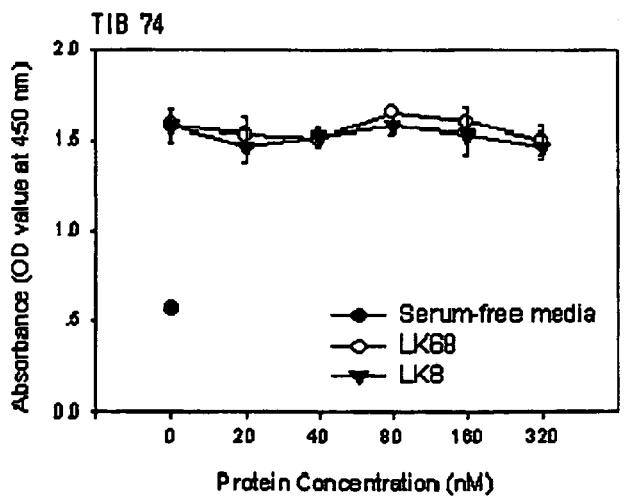
FIG. 5(C) is a graph showing BrdU labelling index of TIB74 cells in the presence of recombinant LK68 and LK8.
Figure 5D:
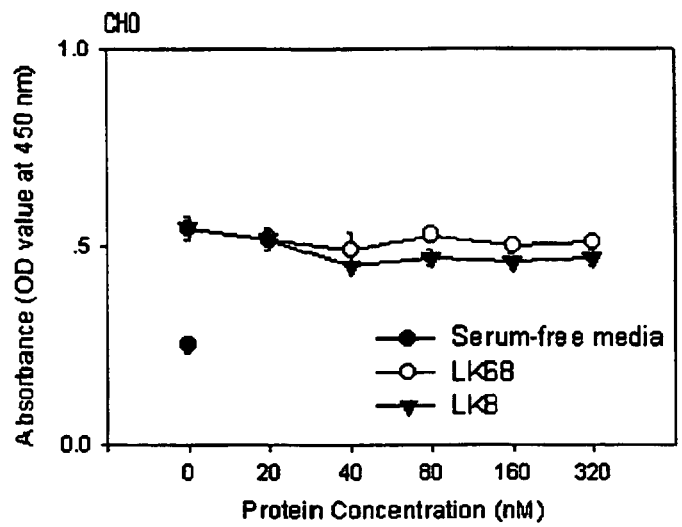
FIG. 5(D) is a graph showing BrdU labelling index of CHO cells in the presence of recombinant LK68 and LK8.
Figure 5E:
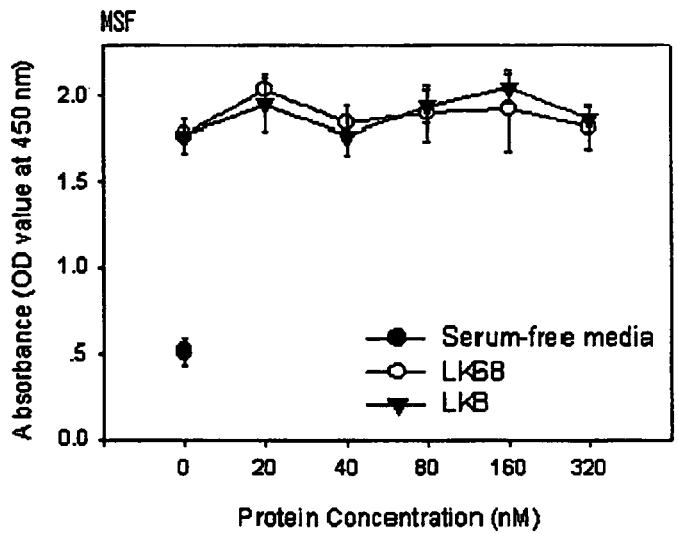
FIG. 5(E) is a graph showing BrdU labelling index of MSF cells in the presence of recombinant LK68 and LK8.
Figure 5F:
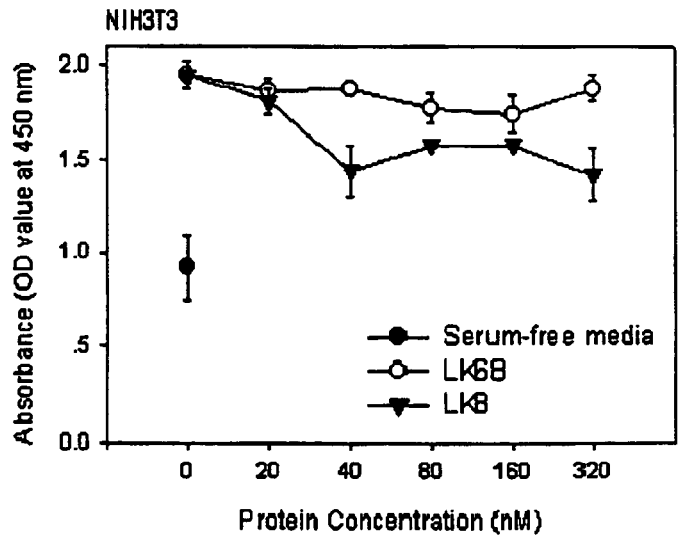
FIG. 5(F) is a graph showing BrdU labelling index of NIH3T3 cells in the presence of recombinant LK68 and LK8.

In the presence of LK68 or single kringle proteins such as LK6, LK7 and LK8, the morphology of BCE or HUVEC cells appeared similar to those of untreated cells. In addition, cell proliferation can be rescued with bFGF stimulation after removal of LK68. These results indicate that LK68 as well as single kringle proteins are not cytotoxic to capillary endothelial cells. Furthermore, the inhibitory activity would appear to be specific for endothelial cells, e.g., BCE and HUVEC cells. Additionally, LK68 as well as LK8 failed to show inhibition of proliferation of non-endothelial cell types, such as CHO cells, mouse skin fibroblast NIH3T3 cells, mouse Lewis lung carcinoma cells, mouse adrenal tumor Y1 cells and mouse embryonic liver/SV40 transformed cell line TIB74(see: FIGS. 5(A) to 5(F)). FIGS. 5(A) to 5(C) represent the sensitivity of various tumor cells such as LLC, Y1, and TIB 74, and FIGS. 5(D) to 5(F) represent the sensitivity of various normal cell lines such as CHO, MSF, and NIH3T3, respectively.

EXAMPLE 5

Inhibition of Endothelial Cell Migration

Cell migration assay was performed in Transwells with 8-mm pores (Costar, USA). Briefly, the wells were coated with fibronectin(25 µg/ml) (Sigma Chemical Co., USA) overnight and HUVECs were plated at a density of 2000/well in 100 µl Dulbecco's modified Eagle's medium containing 0.4% fetal calf serum(FCS) in the upper chamber. 500 µl of DMEM containing 0.4% FCS was added to the lower chamber and incubated at 37° C. for 1 hr. The test samples of 1 µM concentration were added to the upper chamber and 25 ng/ml of bFGF was added to the lower chamber. After 5 hr incubation, cells that crossed the fibronectin-plated membrane were quantified after wiping off the cells in the upper chamber with a cotton swab. The cells across the membrane were stained with Diff-Quik stain set according to the manufacturer's instruction (Dade Behring Inc., USA) and were counted at 100× magnification. The experiments were performed in duplicate.

Figure 6A:
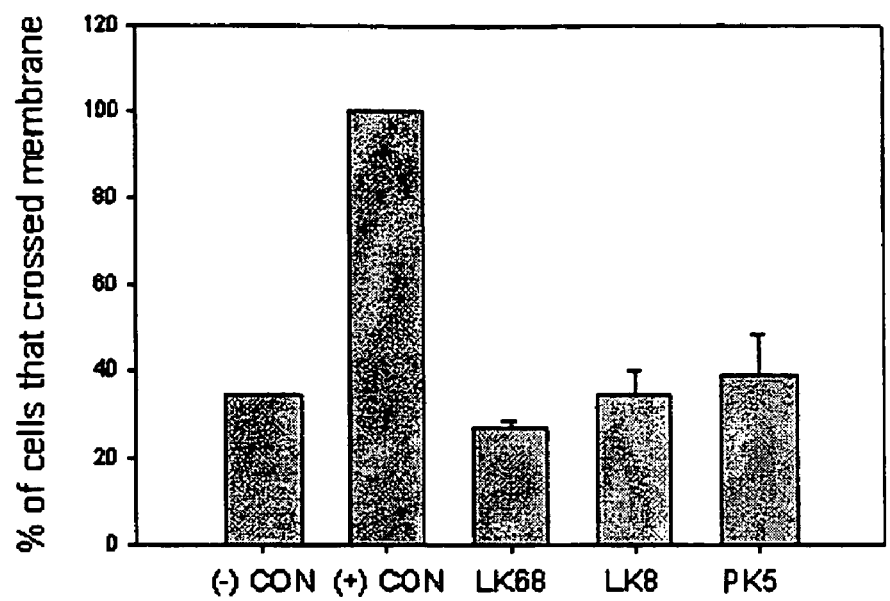
FIG. 6(A) is a graph showing inhibition of HUVEC cell migration by recombinant LK68, LK8 and PK5.
Figure 6B:
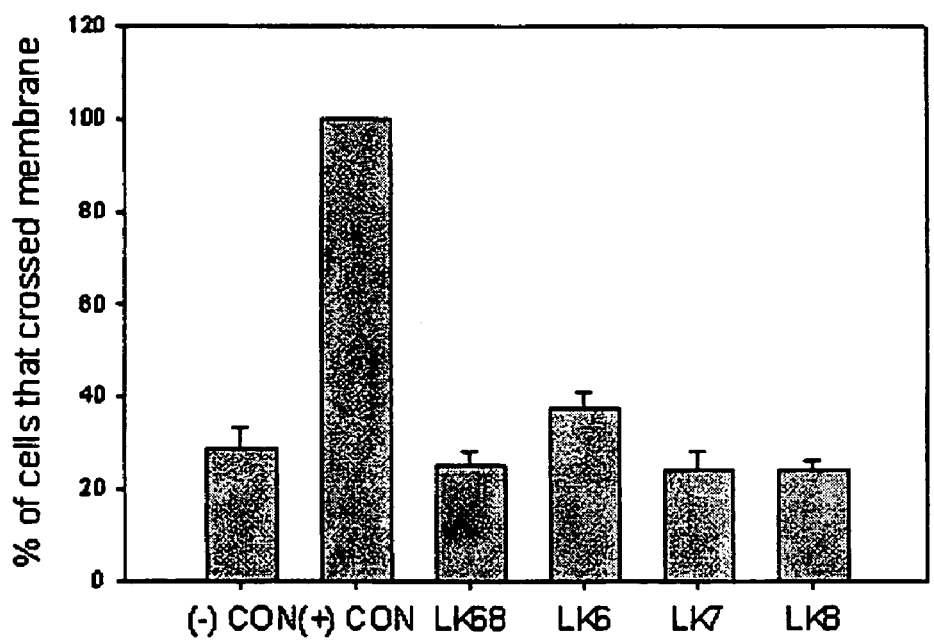
FIG. 6(B) is a graph showing inhibition of HUVEC cell migration by recombinant LK68, LK6, LK7 and LK8.

Basic FGF(25 ng/ml) was used to stimulate the migration of HUVEC cells. With the dose of 1 µM, LK68 as well as single kringle proteins such as LK6, LK7 and LK8 completely inhibited the bFGF-induced HUVEC cell migration to the level of uninduced control(see: FIGS. 6(A) and 6(B)). In FIG. 6, (–)CON represent uninduced control, and (+)CON represent bFGF-induced positive control.

Figure 7:
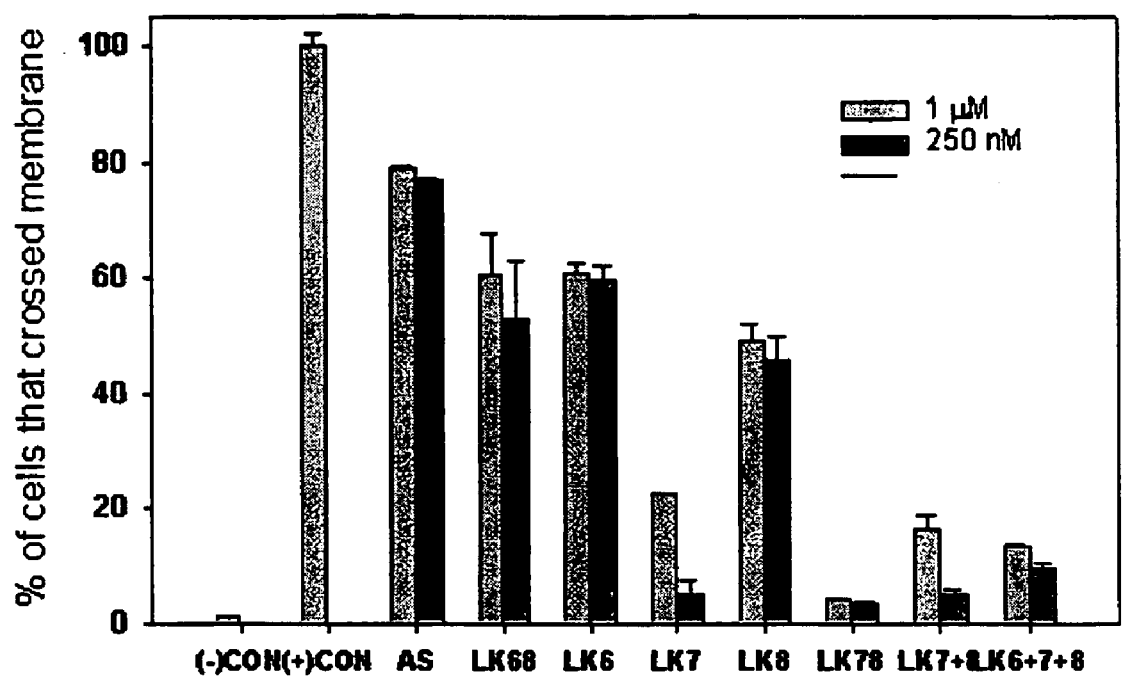
FIG. 7 is a graph showing inhibition of BCE cell migration by angiostatin, recombinant LK68, LK6, LK7, and LK8 and combination of single kringles.

Migration assay using BCE cells was performed as described above. Two different concentrations of LK68 or single kringle proteins applied and all the Apo(a) kringle proteins tested showed inhibitory effects on BCE cell migration. In addition, LK68 and its single kringle proteins were more effective on the inhibition of BCE cell migration than angiostatin(AS) (see: FIG. 7).

EXAMPLE 6

Suppression of Primary Tumor Growth

EXAMPLE 6-1

Lewis Lung Carcinoma

Figure 8:
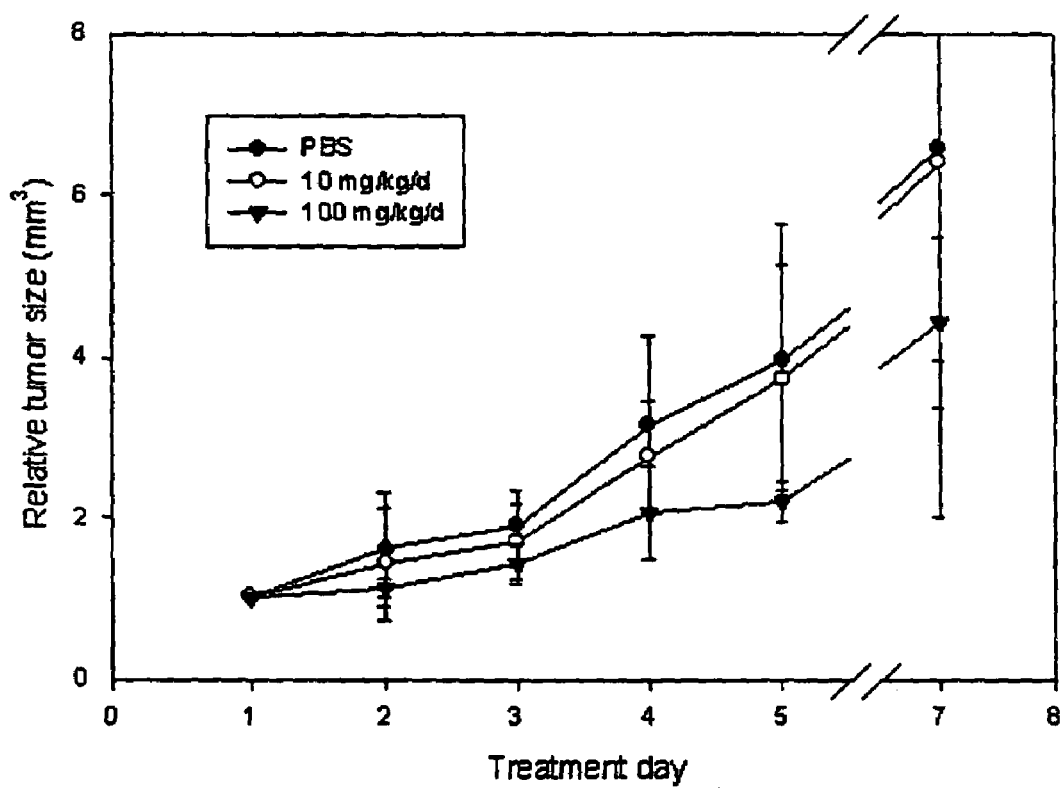
FIG. 8 shows the effect of administration of LK68 to mice having implanted Lewis lung carcinoma cells on total volume as a function of time.

Male 6 to 8-week-old C57BL6/J mice were implanted with Lewis lung carcinomas. The subcutaneous dorsa of mice in the proximal midline were injected with $1\times10^6$ cells in 0.1 ml of saline. When the tumors reached about 5 mm in diameter, tumor-bearing mice received LK68(100 mg/kg body weight) as a suspension in PBS injected subcutaneously at a site distant from the tumor. The control group of mice had only a sham procedure and was treated with PBS only. Tumor size was measured every day during the treatment; and, volumes were determined using the formula width$^2$×length×0.52 and the ratio of treated to control tumor volume(T/C) was determined for the last time point. Treatments were continued for 8 days, at which point all mice were sacrificed and the tumors were removed(see: FIG. 8). As can be seen in FIG. 8, it was clearly determined that the growth of LLC primary tumors was potently suppressed by systemic LK68 therapy; LK68 at a dose of 100 mg/kg caused significant regression of tumor burden only with 7 day treatment.

Figure 9A:
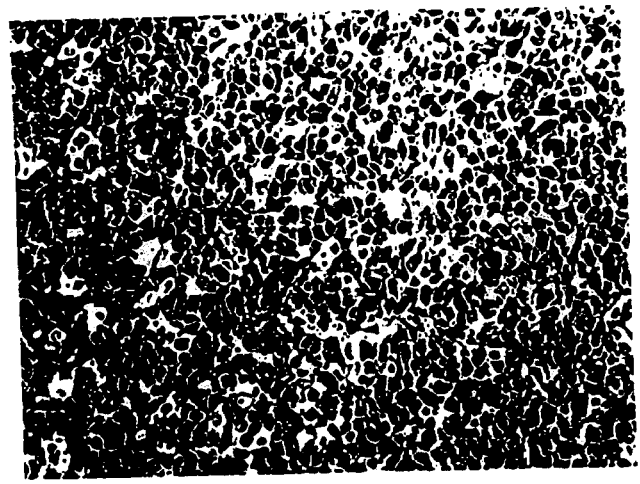
FIGS. 9(A) to 9(C) are photographs showing histological analyses of Lewis lung carcinoma cells by hematoxylin and eosin (H/E) staining.
Figure 9B:
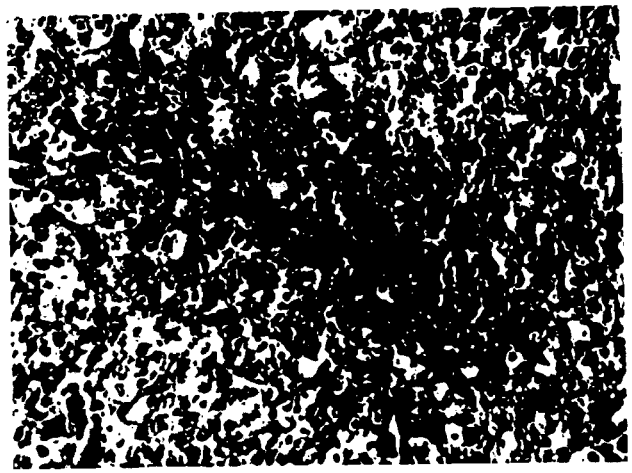
Figure 9C:
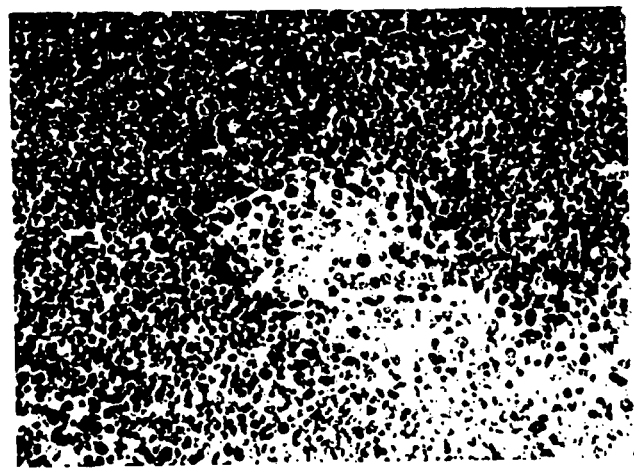

Histological analyses were also carried out to compare tumors from treated and control mice in terms of vessel density and hemorrhage formation, and morphological appearance(see: FIGS. 9(A) to 9(C)). In FIGS. 9(A) to 9(C), 9(A) shows PBS-treated control, 9(B) LLC tumors of 10 mg/kg body weight LK68-treated, and 9(C) LLC tumor of 100 mg/kg body weight LK68-treated, respectively. Obvious histological differences were observed in LK68-treated tumors by hemotoxylin and eosin(H/E) staining: that is tumor cells were not intact and morphologically not viable; and, zonal necrosis was examined around the tumors. Also, vessel density within LK68-treated tumors was reduced. There was no evidence of inflammation or bleeding in any of the mice treated with the recombinant LK68.

EXAMPLE 6-2

Human Lung Carcinoma

Four-week-old outbred female nu/nu nude mice used in this experiment were housed in a sterile environment. Cages, bedding, food and water were all autoclaved. The mice were maintained on a 12-hr light/12-hr dark cycle. Human lung cancer cells (A549 purchased from Korean Cell Line Bank) were maintained in RPMI 1640 medium, supplemented with 10% heat-inactivated FBS and antibiotics. Approximately $2 \times 10^7$ cells of A549 human lung carcinoma were subcutaneously injected into nude mice into the proximal midline of the dorsa. When tumors were palpable at day 7 after tumor implantation, the mice were treated with LK68 at the dose of 100 mg/kg body weight. The control group was treated with PBS only. The treatment was continued for 17 days. The tumor size was measured every other day.

Figure 10:
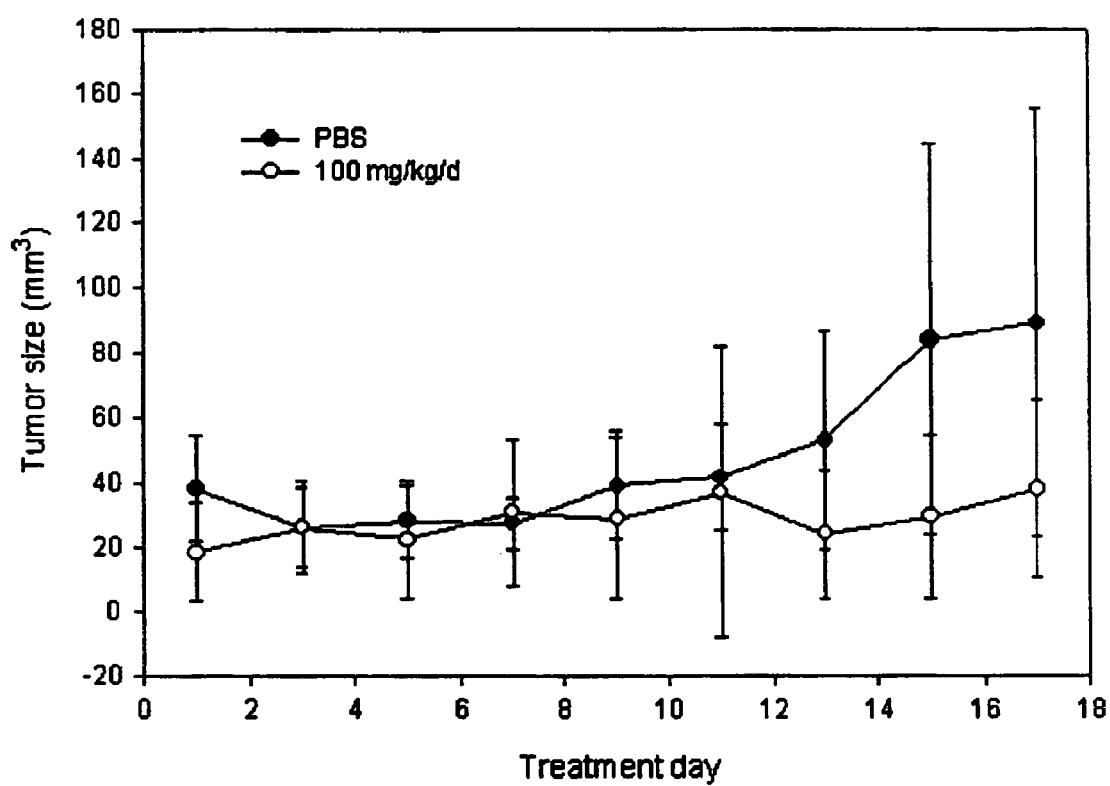
FIG. 10 shows the effect of administration of LK68 to nude mice having implanted human lung carcinoma A549 cells on total volume as a function of time.

The tumor growth was regressed by the LK68 treatment: that is, LK68-treated A549 tumors were approximately 57.5% smaller than tumors in control animals(see: FIG. 10). There was no evidence of any toxicity in any of the treated mice. Continued therapy maintained the tumors in a state of dormancy for as long as it was administered. These data strongly suggest that the anti-angiogenic effect of LK68 can be used to target a wide variety of primary malignancies.

As clearly illustrated and demonstrated as above, the present invention provides a novel angiogenesis inhibitor, LK68 whose amino acid sequence is identical with the human apo(a) kringle domains IV36, IV37 and V38, a DNA sequence encoding the LK68, a recombinant expression vector comprising the DNA, a recombinant microorganism transformed with the recombinant expression vector, use of the LK68 as an anticancer agent, and a method for treating angiogenesis-mediated disease.

What is claimed is:

1. An isolated cDNA which encodes for LK6 protein consisting of SEQ ID NO: 4.
2. An isolated cDNA which encodes for LK7 protein consisting of SEQ ID NO: 6.
3. An isolated cDNA which encodes for LK8 protein consisting of SEQ ID NO: 8.
4. An isolated cDNA which encodes for LK68 protein consisting of SEQ ID NO: 2.
5. The isolated cDNA according to claim 1, wherein the nucleotide sequence of the cDNA is SEQ ID NO: 3.
6. The isolated cDNA according to claim 2, wherein the nucleotide sequence of the cDNA is SEQ ID NO: 5.
7. The isolated cDNA according to claim 3, wherein the nucleotide sequence of the cDNA is SEQ ID NO: 7.
8. The isolated cDNA according to claim 4, wherein the nucleotide sequence of the cDNA is SEQ ID NO: 1.
9. A recombinant expression vector comprising the isolated cDNA of claim 1.
10. A recombinant expression vector comprising the isolated cDNA of claim 2.
11. A recombinant expression vector comprising the isolated cDNA of claim 3.
12. A recombinant expression vector comprising the isolated cDNA of claim 4.
13. The recombinant expression vector according to claim 9, wherein the recombinant expression vector is pET15bILK6 deposited under accession no. KCTC0655BP.
14. The recombinant expression vector according to claim 10, wherein the recombinant expression vector is pET15b/LK7 deposited under accession no. KCTC0656BP.
15. The recombinant expression vector according to claim 11, wherein the recombinant expression vector is pET15b/LK8 deposited under accession no. KCTC0634BP.
16. The recombinant expression vector according to claim 12, wherein the recombinant expression vector is pET11a/LK68 deposited under accession no. KCTC0633BP.
17. A microorganism which is transformed with the recombinant expression vector of claim 9.
18. A microorganism which is transformed with the recombinant expression vector of claim 10.
19. A microorganism which is transformed with the recombinant expression vector of claim 11.
20. A microorganism which is transformed with the recombinant expression vector of claim 12.

* * * * *

SEQUENCE LISTING

<160> NUMBER OF SEQ ID NOS: 14

<210> SEQ ID NO 1
<211> LENGTH: 924
<212> TYPE: DNA
<213> ORGANISM: Homo sapiens

<400> SEQUENCE: 1

```
aaaagccctg tggtccagga ttgctaccat ggtgatggac ggagttatcg aggcatatcc      60
tccaccactg tcacaggaag gacctgtcaa tcttggtcat ctatgatacc acactggcat     120
cagaggaccc cagaaaacta cccaaatgct ggcctgaccg agaactactg caggaatcca     180
gattctggga acaaccctg tgttacaca accgatccgt gtgtgaggtg ggagtactgc      240
aatctgacac aatgctcaga aacagaatca ggtgtcctag agactccac tgttgttcca     300 gttccaagca tggaggctca ttctgaagca gcaccaactg agcaaacccc tgtggtccgc     360
cagtgctacc atggcaatgg ccagagttat cgaggcacat tctccaccac tgtcacagga     420
aggacatgtc aatcttggtc atccatgaca ccacaccggc atcagaggac cccagaaaac     480
tacccaaatg atggcctgac aatgaactac tgcaggaatc cagatgccga tacaggccct     540
tggtgtttta ccacggaccc cagcatcagg tgggagtact gcaacctgac gcgatgctca     600
gacacagaag ggactgtggt cgctcctccg actgtcatcc aggttccaag cctagggcct     660
ccttctgaac aagactgtat gtttgggaat gggaaggat accggggcaa gaaggcaacc     720
actgttactg ggacgccatg ccaggaatgg gctgcccagg agccccatag acacagcacg     780
ttcattccag ggacaaataa atgggcaggt ctggaaaaaa attactgccg taaccctgat     840
ggtgacatca atggtccctg gtgctacaca atgaatccaa gaaaactttt tgactactgt     900
gatatccctc tctgtgcatc ctct                                           924
```

<210> SEQ ID NO 2
<211> LENGTH: 308
<212> TYPE: PRT
<213> ORGANISM: Homo sapiens

<400> SEQUENCE: 2

```
Lys Ser Pro Val Val Gln Asp Cys Tyr His Gly Asp Gly Arg Ser Tyr
 1               5                  10                  15
```

-continued

Arg Gly Ile Ser Ser Thr Thr Val Thr Gly Arg Thr Cys Gln Ser Trp
            20                  25                  30

Ser Ser Met Ile Pro His Trp His Gln Arg Thr Pro Glu Asn Tyr Pro
            35                  40                  45

Asn Ala Gly Leu Thr Glu Asn Tyr Cys Arg Asn Pro Asp Ser Gly Lys
        50                  55                  60

Gln Pro Trp Cys Tyr Thr Thr Asp Pro Cys Val Arg Trp Glu Tyr Cys
65                  70                  75                  80

Asn Leu Thr Gln Cys Ser Glu Thr Glu Ser Gly Val Leu Glu Thr Pro
                85                  90                  95

Thr Val Val Pro Val Pro Ser Met Glu Ala His Ser Glu Ala Ala Pro
            100                 105                 110

Thr Glu Gln Thr Pro Val Val Arg Gln Cys Tyr His Gly Asn Gly Gln
            115                 120                 125

Ser Tyr Arg Gly Thr Phe Ser Thr Thr Val Thr Gly Arg Thr Cys Gln
    130                 135                 140

Ser Trp Ser Ser Met Thr Pro His Arg His Gln Arg Thr Pro Glu Asn
145                 150                 155                 160

Tyr Pro Asn Asp Gly Leu Thr Met Asn Tyr Cys Arg Asn Pro Asp Ala
                165                 170                 175

Asp Thr Gly Pro Trp Cys Phe Thr Thr Asp Pro Ser Ile Arg Trp Glu
            180                 185                 190

Tyr Cys Asn Leu Thr Arg Cys Ser Asp Thr Glu Gly Thr Val Val Ala
        195                 200                 205

Pro Pro Thr Val Ile Gln Val Pro Ser Leu Gly Pro Pro Ser Glu Gln
    210                 215                 220

Asp Cys Met Phe Gly Asn Gly Lys Gly Tyr Arg Gly Lys Lys Ala Thr
225                 230                 235                 240

Thr Val Thr Gly Thr Pro Cys Gln Glu Trp Ala Ala Gln Glu Pro His
            245                 250                 255

Arg His Ser Thr Phe Ile Pro Gly Thr Asn Lys Trp Ala Gly Leu Glu
            260                 265                 270

Lys Asn Tyr Cys Arg Asn Pro Asp Gly Asp Ile Asn Gly Pro Trp Cys
        275                 280                 285

Tyr Thr Met Asn Pro Arg Lys Leu Phe Asp Tyr Cys Asp Ile Pro Leu
    290                 295                 300

Cys Ala Ser Ser
305

<210> SEQ ID NO 3
<211> LENGTH: 273
<212> TYPE: DNA
<213> ORGANISM: Homo sapiens

<400> SEQUENCE: 3
aaaagccctg tggtccagga ttgctaccat ggtgatggac ggagttatcg aggcatatcc      60
tccaccactg tcacaggaag gacctgtcaa tcttggtcat ctatgatacc acactggcat    120
cagaggaccc cagaaaacta cccaaatgct ggcctgaccg agaactactg caggaatcca    180
gattctggga acaaccctg gtgttacaca accgatccgt gtgtgaggtg ggagtactgc     240
aatctgacac aatgctcaga aacagaatca ggt                                 273

<210> SEQ ID NO 4
<211> LENGTH: 91
<212> TYPE: PRT

<213> ORGANISM: Homo sapiens

<400> SEQUENCE: 4

| Lys | Ser | Pro | Val | Val | Gln | Asp | Cys | Tyr | His | Gly | Asp | Arg | Ser | Tyr |
|---|---|---|---|---|---|---|---|---|---|---|---|---|---|---|
| 1 | | | | 5 | | | | | 10 | | | | | 15 |

| Arg | Gly | Ile | Ser | Ser | Thr | Thr | Val | Thr | Gly | Arg | Thr | Cys | Gln | Ser | Trp |
|---|---|---|---|---|---|---|---|---|---|---|---|---|---|---|---|
| | | | | 20 | | | | | 25 | | | | | 30 | |

Ser Ser Met Ile Pro His Trp His Gln Arg Thr Pro Glu Asn Tyr Pro
            35                  40                  45

Asn Ala Gly Leu Thr Glu Asn Tyr Cys Arg Asn Pro Asp Ser Gly Lys
        50                  55                  60

Gln Pro Trp Cys Tyr Thr Thr Asp Pro Cys Val Arg Trp Glu Tyr Cys
65                  70                  75                  80

Asn Leu Thr Gln Cys Ser Glu Thr Glu Ser Gly
                85                  90

<210> SEQ ID NO 5
<211> LENGTH: 267
<212> TYPE: DNA
<213> ORGANISM: Homo sapiens

<400> SEQUENCE: 5

```
gtccgccagt gctaccatgg caatggccag agttatcgag gcacattctc caccactgtc      60
acaggaagga catgtcaatc ttggtcatcc atgacaccac accggcatca gaggacccca     120
gaaaactacc caaatgatgg cctgacaatg aactactgca ggaatccaga tgccgataca     180
ggcccttggt gttttaccac ggaccccagc atcaggtggg agtactgcaa cctgacgcga     240
tgctcagaca cagaagggac tgtggtc                                          267
```

<210> SEQ ID NO 6
<211> LENGTH: 89
<212> TYPE: PRT
<213> ORGANISM: Homo sapiens

<400> SEQUENCE: 6

Val Arg Gln Cys Tyr His Gly Asn Gly Gln Ser Tyr Arg Gly Thr Phe
1               5                   10                  15

Ser Thr Thr Val Thr Gly Arg Thr Cys Gln Ser Trp Ser Ser Met Thr
            20                  25                  30

Pro His Arg His Gln Arg Thr Pro Glu Asn Tyr Pro Asn Asp Gly Leu
        35                  40                  45

Thr Met Asn Tyr Cys Arg Asn Pro Asp Ala Asp Thr Gly Pro Trp Cys
    50                  55                  60

Phe Thr Thr Asp Pro Ser Ile Arg Trp Glu Tyr Cys Asn Leu Thr Arg
65                  70                  75                  80

Cys Ser Asp Thr Glu Gly Thr Val Val
                85

<210> SEQ ID NO 7
<211> LENGTH: 258
<212> TYPE: DNA
<213> ORGANISM: Homo sapiens

<400> SEQUENCE: 7

```
gaacaggact gcatgtttgg gaatgggaaa ggataccggg gcaagaaggc aaccactgtt      60
actgggacgc catgccagga atgggctgcc caggagcccc atagacacag cacgttcatt     120
ccagggacaa ataatgggc aggtctggaa aaaaattact gccgtaaccc tgatggtgac     180
```

```
atcaatggtc cctggtgcta cacaatgaat ccaagaaaac tttttgacta ctgtgatatc    240
cctctctgtg catcctct                                                  258
```

<210> SEQ ID NO 8
<211> LENGTH: 86
<212> TYPE: PRT
<213> ORGANISM: Homo sapiens

<400> SEQUENCE: 8

```
Glu Gln Asp Cys Met Phe Gly Asn Gly Lys Gly Tyr Arg Gly Lys Lys
 1               5                  10                  15

Ala Thr Thr Val Thr Gly Thr Pro Cys Gln Glu Trp Ala Ala Gln Glu
                20                  25                  30

Pro His Arg His Ser Thr Phe Ile Pro Gly Thr Asn Lys Trp Ala Gly
            35                  40                  45

Leu Glu Lys Asn Tyr Cys Arg Asn Pro Asp Gly Asp Ile Asn Gly Pro
        50                  55                  60

Trp Cys Tyr Thr Met Asn Pro Arg Lys Leu Phe Asp Tyr Cys Asp Ile
65                  70                  75                  80

Pro Leu Cys Ala Ser Ser
                85
```

<210> SEQ ID NO 9
<211> LENGTH: 29
<212> TYPE: DNA
<213> ORGANISM: Artificial Sequence
<220> FEATURE:
<223> OTHER INFORMATION: single standed oligonucleotide

<400> SEQUENCE: 9

```
tccatatgaa aagccctgtg gtccaggat                                       29
```

<210> SEQ ID NO 10
<211> LENGTH: 33
<212> TYPE: DNA
<213> ORGANISM: Artificial Sequence
<220> FEATURE:
<223> OTHER INFORMATION: single stranded oligonucleotide

<400> SEQUENCE: 10

```
cagtccatat ggtccgccag tgctaccatg gca                                  33
```

<210> SEQ ID NO 11
<211> LENGTH: 31
<212> TYPE: DNA
<213> ORGANISM: Artificial Sequence
<220> FEATURE:
<223> OTHER INFORMATION: single stranded olgonucleotide

<400> SEQUENCE: 11

```
ggaattccat atggaacagg actgcatgtt t                                    31
```

<210> SEQ ID NO 12
<211> LENGTH: 26
<212> TYPE: DNA
<213> ORGANISM: Artificial Sequence
<220> FEATURE:
<223> OTHER INFORMATION: single stranded oligonucleotide

<400> SEQUENCE: 12

```
cgggatcctt aacctgattc tgtttc                                          26
```

```
<210> SEQ ID NO 13
<211> LENGTH: 26
<212> TYPE: DNA
<213> ORGANISM: Artificial Sequence
<220> FEATURE:
<223> OTHER INFORMATION: single stranded oligonucleotide

<400> SEQUENCE: 13
cgggatcctt agaccacagt cccttc                                              26

<210> SEQ ID NO 14
<211> LENGTH: 23
<212> TYPE: DNA
<213> ORGANISM: Artificial Sequence
<220> FEATURE:
<223> OTHER INFORMATION: single stranded oligonucleotide

<400> SEQUENCE: 14
cgggatcctt aagaggatgc aca                                                 23
```